(12) United States Patent
Schwandt et al.

(10) Patent No.: US 7,776,139 B2
(45) Date of Patent: Aug. 17, 2010

(54) SEPARATOR WITH TRANSFER TUBE DRAINAGE

(75) Inventors: Brian W. Schwandt, Fort Atkinson, WI (US); Christopher E. Holm, Madison, WI (US); Mark V. Holzmann, Stoughton, WI (US); Michael J. Connor, Stoughton, WI (US)

(73) Assignee: Cummins Filtration IP, Inc., Minneapolis, MN (US)

( * ) Notice: Subject to any disclaimer, the term of this patent is extended or adjusted under 35 U.S.C. 154(b) by 268 days.

(21) Appl. No.: 12/026,720

(22) Filed: Feb. 6, 2008

(65) Prior Publication Data

US 2009/0193972 A1 Aug. 6, 2009

(51) Int. Cl.
*B01D 46/00* (2006.01)

(52) U.S. Cl. .............................. 95/268; 95/273; 95/286; 55/319; 55/320; 55/324; 55/330; 55/423; 55/484; 55/466; 55/DIG. 19

(58) Field of Classification Search ................... 55/330, 55/423, 319, 320, 323, 324, 466, 484, 482, 55/DIG. 19; 95/273, 268, 286
See application file for complete search history.

(56) References Cited

U.S. PATENT DOCUMENTS

| | | | |
|---|---|---|---|
| 2,252,242 A | 8/1941 | Wood | |
| 4,861,359 A | 8/1989 | Tettman | |
| 5,170,640 A * | 12/1992 | Heitmann et al. | ............. 24/284 |
| 5,438,965 A | 8/1995 | Aronsson et al. | |
| 5,902,362 A | 5/1999 | Paoluccio | |
| 6,143,049 A | 11/2000 | Gieseke et al. | |
| 6,247,463 B1 | 6/2001 | Fedorowicz et al. | |
| 6,279,556 B1 | 8/2001 | Busen et al. | |
| 6,290,738 B1 | 9/2001 | Holm | |
| 6,309,436 B1 | 10/2001 | Holch | |
| 6,354,283 B1 | 3/2002 | Hawkins et al. | |
| 6,478,018 B2 | 11/2002 | Fedorowicz et al. | |
| 6,478,019 B2 | 11/2002 | Fedorowicz et al. | |
| 6,505,615 B2 | 1/2003 | Pietschner | |
| 6,599,350 B1 | 7/2003 | Rockwell et al. | |
| 6,626,163 B1 | 9/2003 | Busen et al. | |
| 6,684,864 B1 | 2/2004 | Busen et al. | |
| 6,858,051 B2 | 2/2005 | Uhlenbrock | |
| 7,186,282 B2 | 3/2007 | Su | |
| 7,238,216 B2 | 7/2007 | Malgorn et al. | |
| 2001/0047967 A1 * | 12/2001 | Williamson et al. | ......... 210/799 |
| 2004/0040272 A1 | 3/2004 | Uhlenbrock | |

(Continued)

*Primary Examiner*—Duane Smith
*Assistant Examiner*—Tiffany N Palmer
(74) *Attorney, Agent, or Firm*—Andrus, Sceales, Starke & Sawall, LLP; J. Bruce Schelkopf

(57) ABSTRACT

A dual stage coalescer includes a separator in a separator chamber separating gas and liquid by inertial impaction, and a coalescer filter element in a coalescer chamber separating gas and liquid by coalescence. A transfer tube extends between the separator chamber and a downstream subchamber in the coalescer chamber at the downstream face of the coalescer filter element, and supplies pre-separated liquid from the separator chamber through the transfer tube to the noted downstream subchamber as driven by pressure differential between the separator chamber and the downstream subchamber, to eliminate a dedicated housing drain outlet from the separator chamber. The coalescer may provide a crankcase ventilation filter for an internal combustion engine having blowby gas containing an air-oil mixture.

28 Claims, 5 Drawing Sheets

U.S. PATENT DOCUMENTS

| | | |
|---|---|---|
| 2006/0032486 A1 | 2/2006 | Prasad |
| 2006/0059875 A1 | 3/2006 | Malgorn et al. |
| 2006/0062699 A1 | 3/2006 | Evenstad et al. |
| 2006/0086649 A1 | 4/2006 | Wieczorek et al. |
| 2006/0124117 A1 | 6/2006 | Knauf et al. |
| 2007/0240392 A1 | 10/2007 | Ng et al. |
| 2007/0256566 A1 | 11/2007 | Faber et al. |

* cited by examiner

US 7,776,139 B2

SEPARATOR WITH TRANSFER TUBE DRAINAGE

BACKGROUND AND SUMMARY

The invention relates to separators, including impactor separators, and coalescers, including crankcase ventilation filters.

Separators are known in the prior art, including dual stage separation provided by a separator in a separator chamber separating gas and liquid by inertial impaction, and a coalescer filter element in a coalescer chamber separating gas and liquid by coalescence. In internal combustion engine applications having blowby gas containing an air-oil mixture, a crankcase ventilation filter arrangement may have a separator chamber and a coalescer chamber, with a separator in the separator chamber separating air and oil by inertial impaction, and a coalescer filter element in the coalescer chamber separating air and oil by coalescence.

The present invention arose during continuing development efforts related to the above technology. In one aspect, the present system enables elimination of an extra drainage port otherwise needed in the above noted structure. In another aspect, manufacturing and space efficiencies are enabled. The invention also arose from various alternative approaches, including various types of separators, including first and second separation chambers.

DETAILED DESCRIPTION

Figure 1:
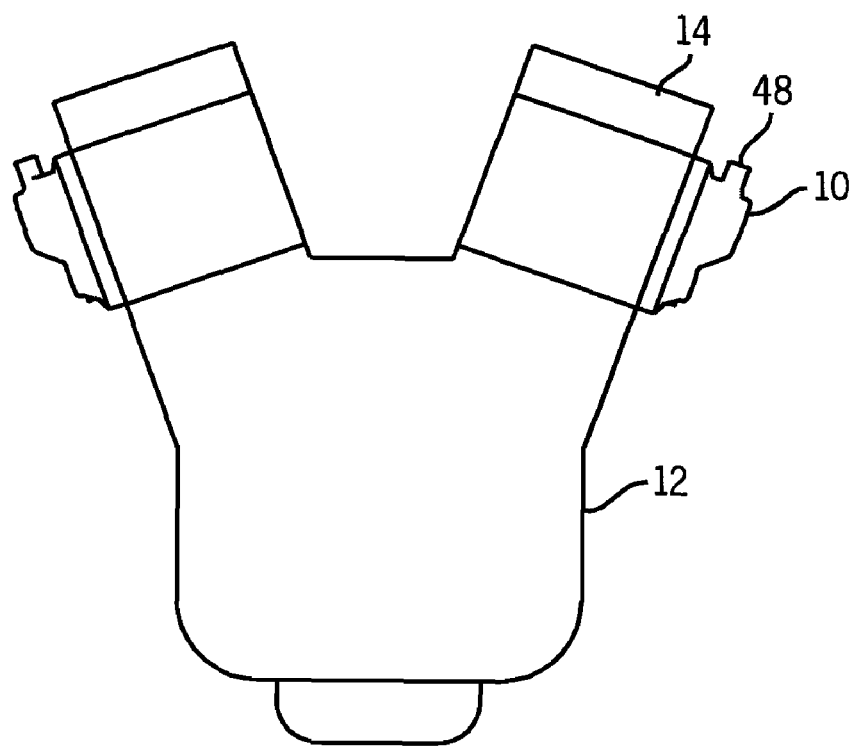
FIG. 1 is a schematic illustration showing a separator in accordance with the invention providing a crankcase ventilation filter for an internal combustion engine.
Figure 3:
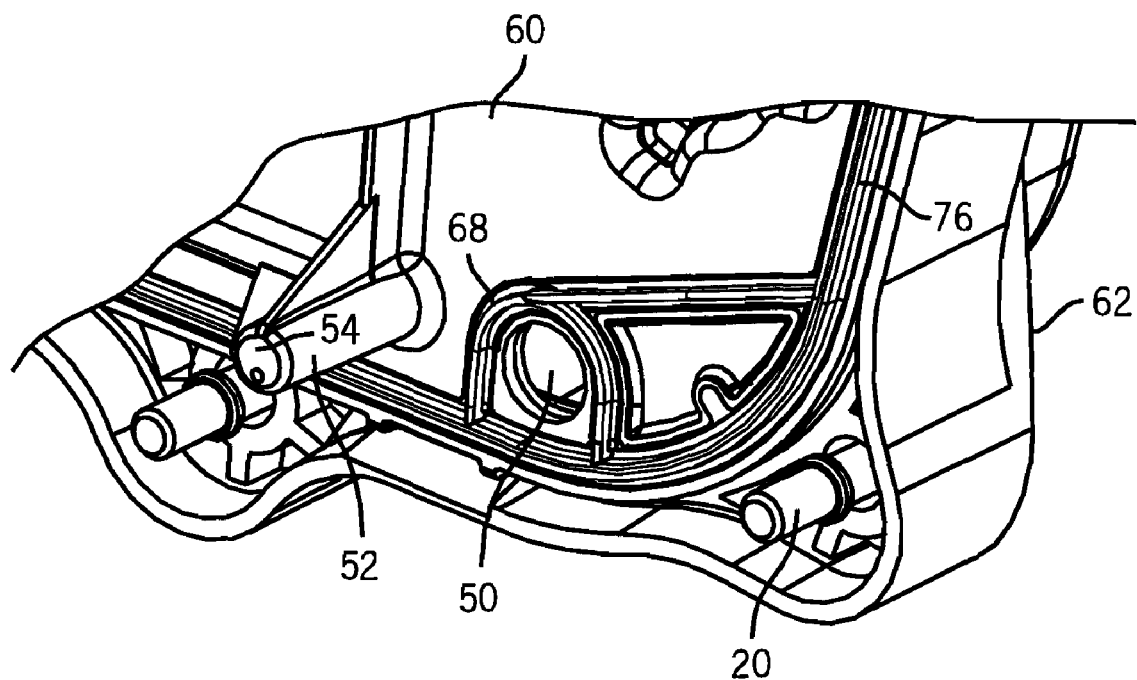
FIG. 3 is an enlarged view of a portion of FIG. 2 taken along line 3-3.

FIG. 1 shows a separator provided by a coalescer 10 mounted on an internal combustion engine 12, for example a V-type engine, and providing a crankcase ventilation filter for the engine's blowby gas containing an air-oil mixture. In one embodiment, coalescer 10 providing the crankcase ventilation filter is mounted along the sloped side of the cylinder or valve head 14. In one embodiment, cylinder head 14 has a blowby port 16, FIG. 6, supplying blowby gas containing an air-oil mixture to the coalescer crankcase ventilation filter 10.

Figure 2:
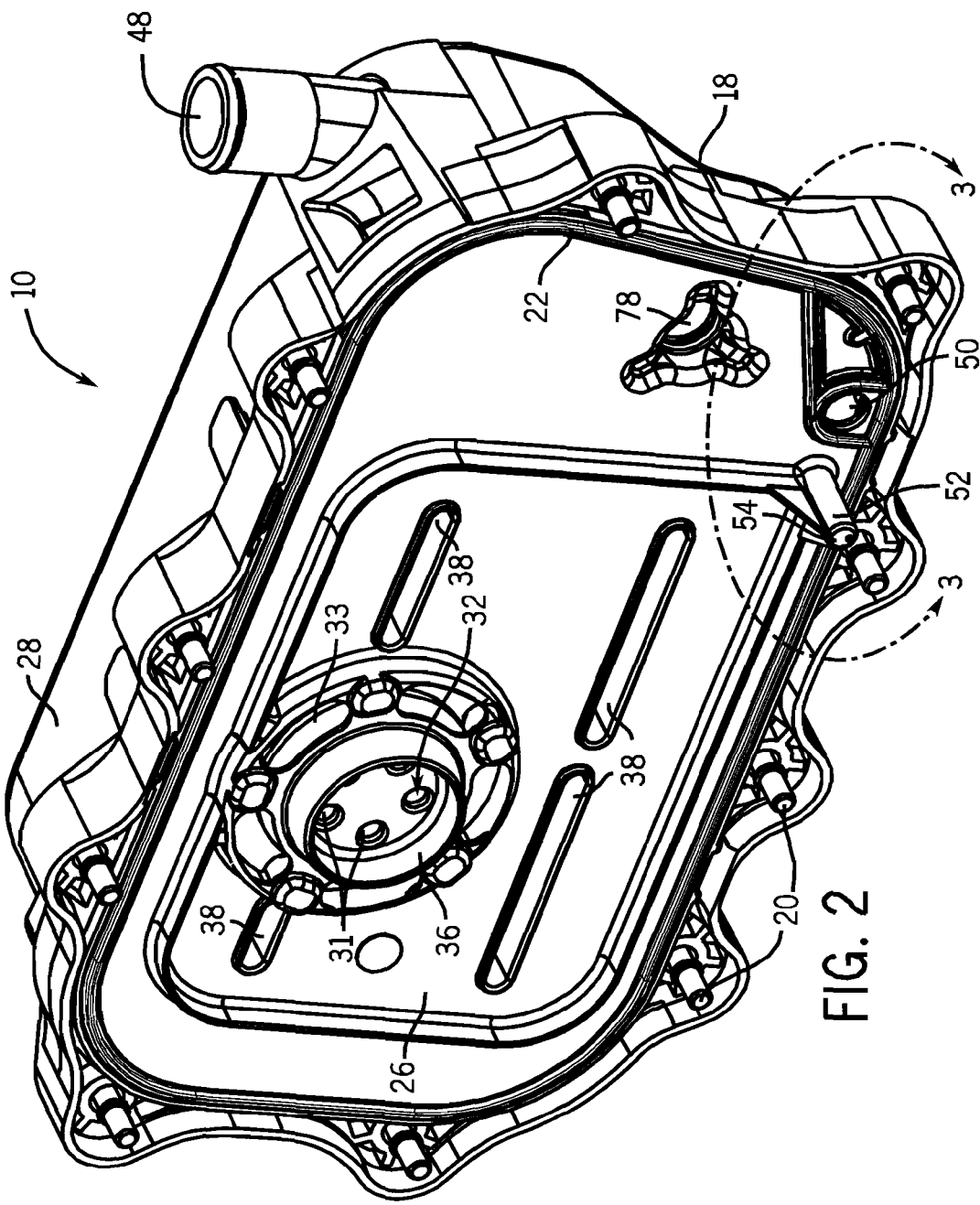
FIG. 2 is a perspective view of the coalescer of FIG. 1 removed from the engine.
Figure 4:
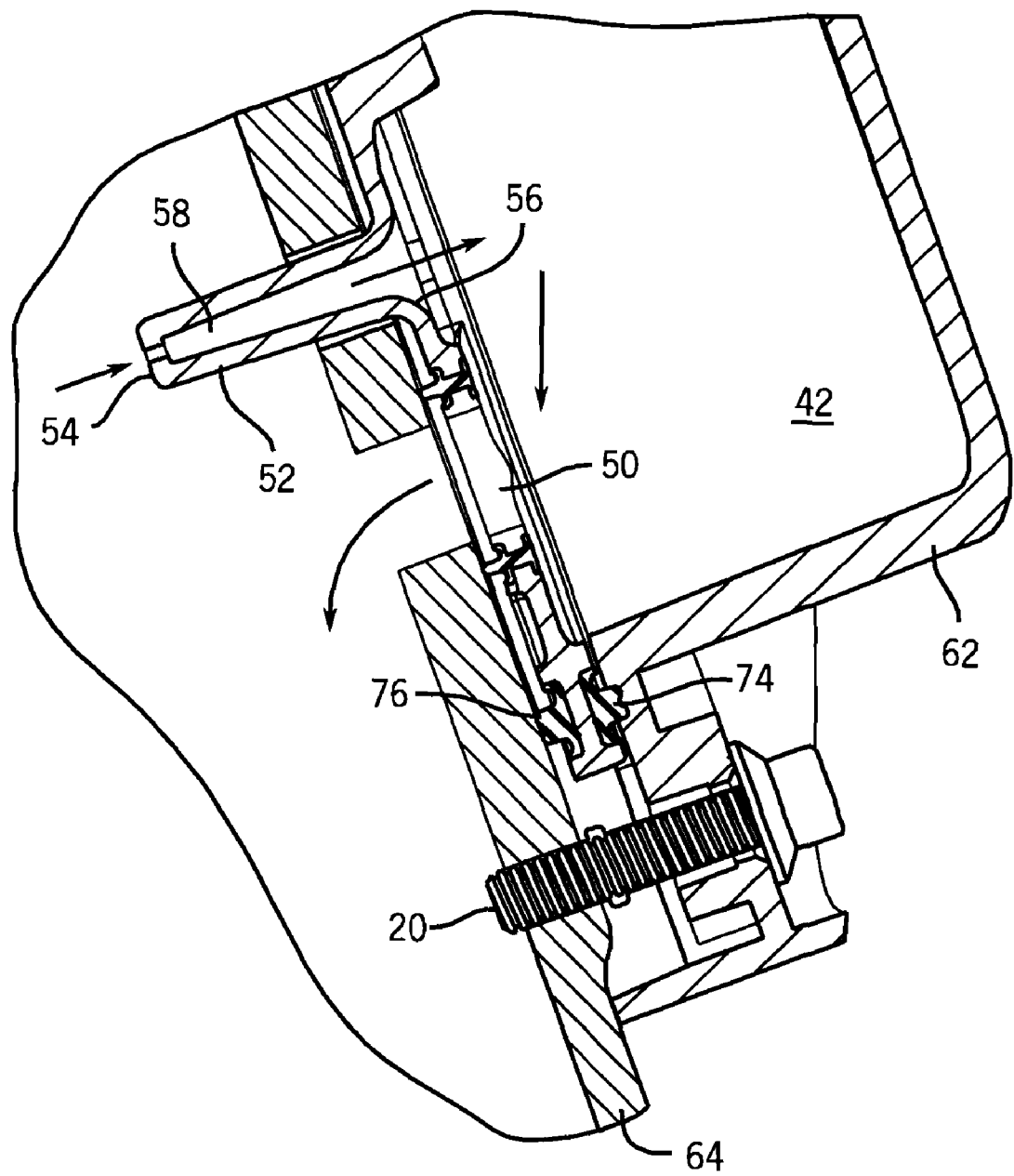
FIG. 4 is a sectional view of a portion of FIG. 2.
Figure 5:
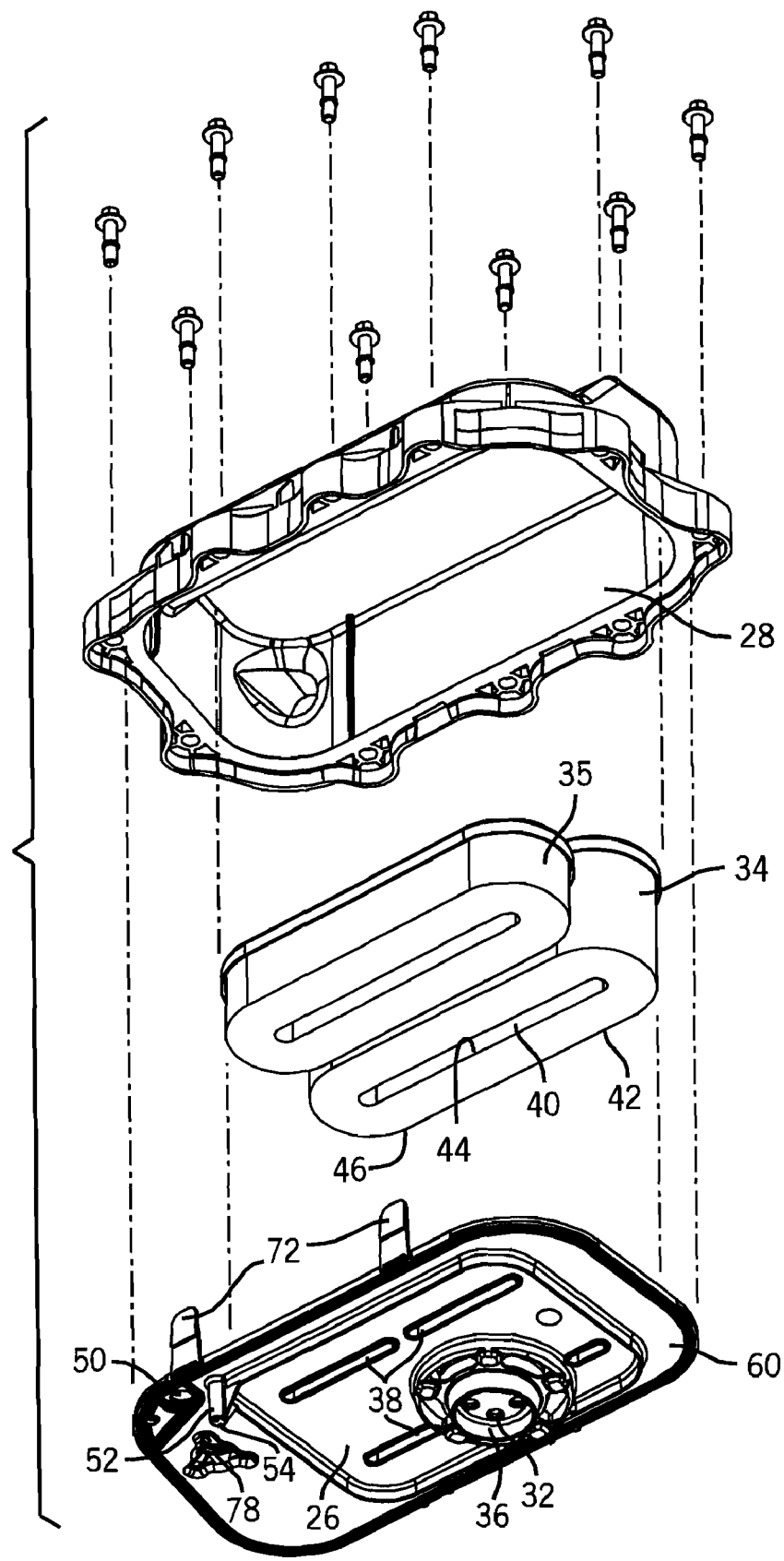
FIG. 5 is an exploded perspective view from below of the separator of FIG. 2.
Figure 6:
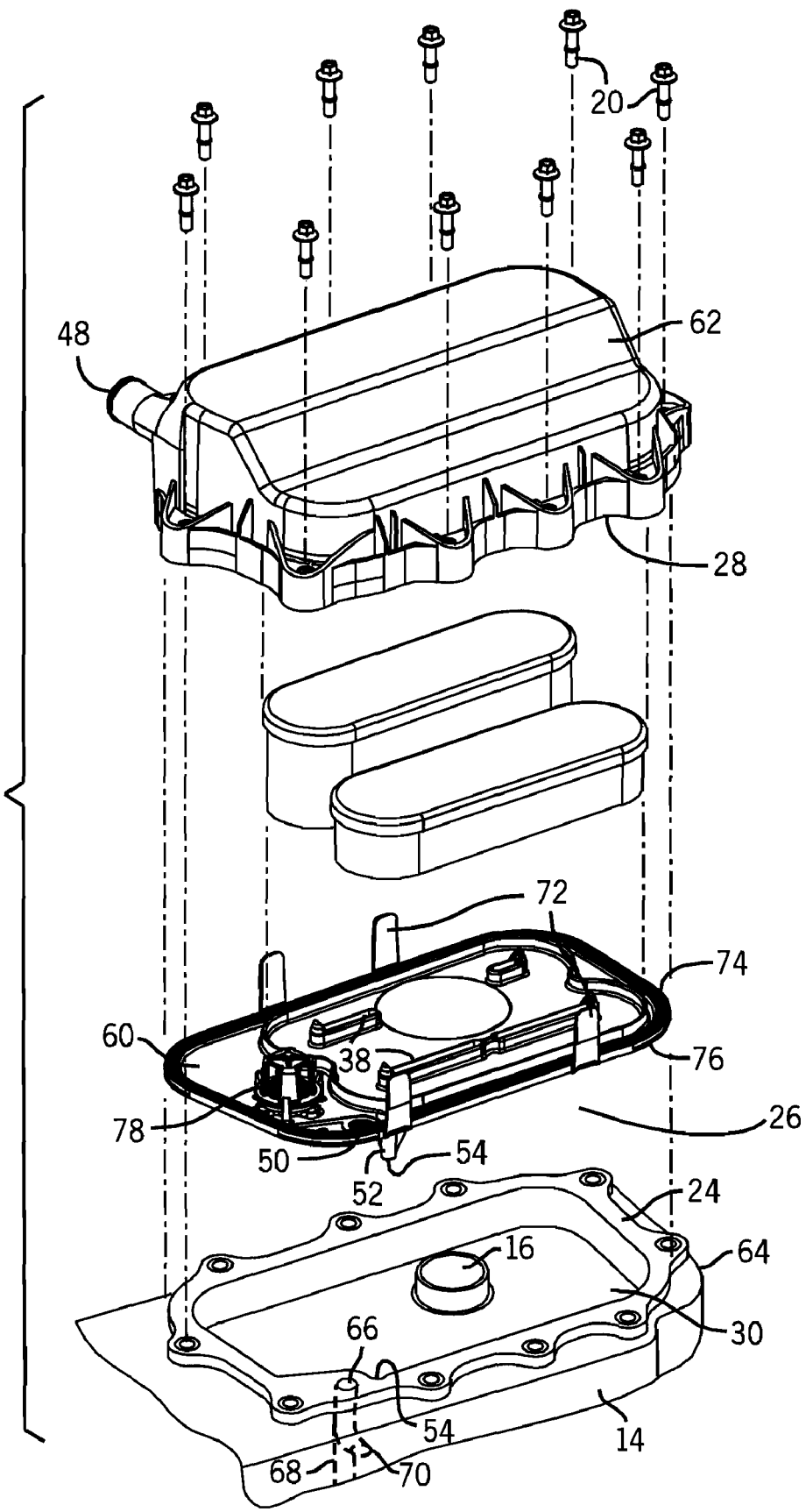
FIG. 6 is an exploded perspective view from above of the separator of FIG. 2.

Crankcase ventilation filter 10 includes a housing 18, FIG. 2, mounted to valve head 14 by bolts such as 20, and sealed thereto at gasket 22 engaging valve head seat 24, FIG. 6. Housing 18 has a separator chamber 26 and a coalescer chamber 28. Valve head 14 may have a well 30 formed in the outer surface thereof which cooperates with housing 18 to also provide separator chamber 26. A separator 32, FIGS. 2, 5, in the separator chamber separates air and oil by inertial impaction, preferably by acceleration through venturis or nozzles 31 against an impactor plate or pad 33. A coalescer filter element, preferably a pair of racetrack shaped coalescer filter elements 34, 35, in coalescer chamber 28 separates air and oil by coalescence. The housing has an air-oil inlet 36 delivering the air-oil mixture from blowby gas port 16 to separator 32 for at least partial pre-separation of air and oil. The housing has one or more transfer passages 38 transferring the partially pre-separated air and oil from separator chamber 26 to coalescer chamber 28. At least a portion of the pre-separated oil remains in separator chamber 26. Each of the coalescer filter elements 34, 35 divide coalescer chamber 28 into an upstream subchamber such as 40 and a downstream subchamber such as 42. The pre-separated air and oil flows inside-out through the coalescer filter elements, i.e. from hollow interior subchamber 40 radially outwardly through the respective coalescer filter element to subchamber 42. Each respective coalescer filter element has an upstream face such as 44 facing upstream subchamber 40 and receiving partially pre-separated air and oil through transfer passage 38 from separator chamber 26. Each respective coalescer filter element has a downstream face such as 46 facing downstream chamber 42 and discharging air and separated coalesced oil. The coalesced oil drains along the downstream face 46. The air-oil flow through the housing experiences a pressure drop between separator chamber 26 and downstream subchamber 42. The housing has an air outlet 48 discharging air from downstream subchamber 42, which discharged air may, for example, be routed and fed back to the engine air induction system. The housing has an oil drain outlet 50 draining oil from downstream subchamber 42.

A squirt tube or transfer tube 52, FIGS. 2-6, extends between separator chamber 26 and downstream subchamber 42 and supplies the noted pre-separated oil from separator chamber 26 to downstream subchamber 42 as driven by the noted pressure differential between separator chamber 26 and downstream subchamber 42. Separator chamber 26 preferably has a sloped surface, which may be provided by the undersurface of the housing and/or by the facing surface of well 30 of head 14, guiding the pre-separated oil to a collection zone 54 forming a pool thereat. The sloped surface and the location of the pool are determined by the mounting orientation of the crankcase ventilation filter housing, e.g. FIG. 1 or some other orientation. It is desired that the transfer tube 52 have a lower end 54 extending downwardly into collection zone 54 and submerged in the pre-separated oil when the pool rises above a given level. Transfer tube 52 has an upper end 56 communicating with downstream subchamber 42. Drain outlet 50 drains both: a) coalesced oil from downstream face 46 of coalescer filter element 34 (and the downstream faces of any additional coalescer filter elements such as 35) along a first flow path through downstream subchamber 42; and b) pre-separated oil from separator 32 along a second flow path through separator chamber 26 then through transfer tube 52 along hollow interior passage 58 thereof then through downstream subchamber 42 and joining the coalesced oil along the noted first flow path. The pre-separated oil is discharged from separator chamber 26 through transfer tube 52 without a second drain outlet from the housing otherwise dedicated for such pre-separated oil drainage.

Housing 18 includes a dividing wall 60 between separator chamber 26 and coalescer chamber 28. Transfer passages 38 and transfer tube 52 each extend through dividing wall 60. The dividing wall has a first set of one or more openings 38 therethrough providing the noted one or more transfer passages. The dividing wall has a second opening 58 therethrough providing the upper end of transfer tube 52. The dividing wall has a third opening 50 therethrough providing the noted drain outlet. In one preferred embodiment, housing 18 includes a cover 62 and a base 64, with the base being provided by a portion of cylinder head 14. Separator chamber 26 is in base 64 at well 30 in cylinder head 14. Coalescer chamber 28 is in cover 62. Drain outlet 50 includes a drain passage 66 through base 64 and isolated from separator chamber 26 by gasket portions 68, FIG. 3, between dividing wall 60 and face 24 of head 14. Drain opening 50 through dividing wall 60 communicates with downstream subchamber 42, but not with separator chamber 26. Oil in downstream subchamber 42 drains through drain opening 50 in dividing wall 60 and through drain passage 66 through base 64. In one preferred embodiment, drain passage 66 continues through cylinder head 14 as shown in dashed line at 68 to drain oil back into the engine. In another embodiment, drain passage 66 exits externally of cylinder head 14 as shown in dashed line at 70 to return oil through a return tube or other plumbing to a designated location in the engine.

The system has applicability beyond crankcase ventilation filters to coalescers having a housing having a separator chamber and a coalescer chamber, with a separator in the separator chamber separating gas and liquid by inertial impaction, and a coalescer filter element in the coalescer chamber separating gas and liquid by coalescence. The housing 18 has a gas-liquid inlet 36 delivering a gas-liquid mixture to separator 32 for at least partial pre-separation of the gas and liquid. The housing has one or more transfer passages 38 transferring the partially pre-separated gas and liquid from separator chamber 26 to coalescer chamber 28. At least a portion of the pre-separated liquid remains in separator chamber 26. One or more coalescer filter elements 34, 35 divide the coalescer chamber into an upstream subchamber 40 and a downstream subchamber 42. Each coalescer filter element has an upstream face such as 44 facing upstream subchamber 40 and receiving partially pre-separated gas and liquid through transfer passage 38 from separator chamber 26. Each coalescer filter element has a downstream face 46 facing downstream subchamber 42 and discharging gas and separated coalesced liquid. The gas-liquid flow through the housing experiences a pressure drop between separator chamber 26 and downstream subchamber 42. The housing has a gas outlet 48 discharging gas from downstream subchamber 42. The housing has a drain outlet 50 draining liquid from downstream subchamber 42. Transfer tube 52 extends between separator chamber 26 and downstream subchamber 42 and supplies pre-separated liquid from separator chamber 26 through passage 58 in transfer tube 52 to downstream subchamber 42 as driven by the pressure differential between separator chamber 26 and downstream subchamber 42. The separator chamber 26 has a sloped surface selected as above according to orientation, guiding pre-separated liquid to a collection zone 54 and forming a pool thereat. Transfer tube 52 has lower end 54 extending downwardly into the collection zone and is submerged in the pre-separated liquid when the pool rises above a given level. The transfer tube has an upper end 56 communicating with downstream subchamber 42. Drain outlet 50 drains both: a) coalesced liquid from downstream face 46 of the coalescer filter element along a first flow path through downstream subchamber 42; and b) pre-separated liquid from separator 32 then through transfer tube 52 along passage 58 then through downstream subchamber 42 and joining the noted coalesced liquid along the noted first flow path. The pre-separated liquid is discharged from separator chamber 26 through transfer tube 52 without a second liquid drain outlet from the housing. It is typical that a coalescer with a pre-separator has two liquid drain outlets, namely one drain for the coalescer and another drain for the separator. In one desirable aspect of the present system, the noted second drain is eliminated, and the housing need only have a single drain draining both the coalesced liquid and the separated liquid.

Housing 18 includes the noted dividing wall 60 between separator chamber 26 and coalescer chamber 28. The one or more transfer passages 38 and the transfer tube 52 each extend through dividing wall 60. The dividing wall has a first set of one or more openings 38 therethrough providing the noted one or more transfer passages. The dividing wall has a second opening 58 therethrough providing the noted transfer tube 52. The dividing wall has a third opening 50 therethrough providing the noted drain outlet. Housing 18 preferably includes cover 62 and base 64, with separator chamber 26 in the base, and coalescer chamber 28 in the cover. The noted drain outlet includes drain passage 66 through the base and isolated from the separator chamber. Drain opening 50 in dividing wall 60 communicates with downstream subchamber 42 but not with separator chamber 26. Liquid in downstream subchamber 42 drains through drain opening 50 in dividing wall 60 and through drain passage 66 through base 64. Dividing wall 60 is mounted to cover 62 by snap tabs such as 72. Dividing wall 60 is sealed between cover 62 and base 64 by upper and lower gaskets 74 and 76 compressed between the cover and base upon tightening of bolts 20. Dividing wall 60 may have a pressure relief valve 78 therein which is biased to a normally closed position but opens in response to excessive pressure in separator chamber 26, e.g. upon clogging of filter elements 34, 35, whereby to provide a bypass relief passage, i.e. bypassing the filter elements to allow flow to chamber 28 and outlet 48.

A method is provided for desirably eliminating a second liquid drain outlet in a coalescer having a housing having a separator chamber 26 and a coalescer chamber 28, with a separator 32 in the separator chamber separating gas and liquid by inertial impaction, and a coalescer 34, 35 in the coalescer chamber separating gas and liquid by coalescence. The method includes providing the housing with a gas-liquid inlet 36 delivering a gas-liquid mixture to separator 32 for at least partial pre-separation of the gas and liquid, providing the housing with one or more transfer passages 38 transferring the partially pre-separated gas and liquid from the separator chamber 26 to the coalescer chamber 28, at least a portion of the pre-separated liquid remaining in separator chamber 26. The method includes providing one or more coalescer filter elements 34, 35 dividing the coalescer chamber 28 into an upstream subchamber 40 and a downstream subchamber 42, providing the coalescer filter element with an upstream face 44 facing the upstream subchamber 40 and receiving the partially pre-separated gas and liquid through the transfer passage 38 from separator chamber 26, providing the coalescer filter element with a downstream face 46 facing the downstream subchamber 42 and discharging gas and separated coalesced liquid. The method includes providing the gas-liquid flow through the housing to experience a pressure drop between the separator chamber 26 and the downstream subchamber 42, due to the restriction to flow therebetween including through the coalescer filter element. The method includes providing the housing with a gas outlet 42 discharging gas from the downstream subchamber 42, and providing the housing with a drain outlet 50 draining liquid from the downstream subchamber 42. The method includes providing a squirt tube or transfer tube 52 extending between the separator chamber 26 and the downstream subchamber 42, and supplying the pre-separated liquid from the separator chamber 26 through passage 58 through transfer tube 52 to downstream subchamber 42 as driven by the pressure differential between the separator chamber 26 and the downstream subchamber 42. The method includes providing the separator chamber 26 with the noted sloped surface according to orientation, guiding the pre-separated liquid along such sloped surface to collection zone 54 forming a pool thereat, and providing the transfer tube 52 at a lower end 54 extending downwardly into the collection zone and submerged in the pre-separated liquid when the pool rises above a given level, and providing the transfer tube 52 with an upper end 56 communicating with the downstream subchamber 42. The method includes draining through the drain outlet 50 both: a) coalesced liquid from downstream face 46 of the coalescer filter element along a first flow path through the downstream subchamber 42; and b) pre-separated liquid from the separator 32 along a second flow path through the separator chamber 26 then through transfer tube 52 then through downstream subchamber 42 and joining with the coalesced liquid along the noted first flow path. In one desirable embodiment, the method includes discharging the pre-separated liquid from the separator chamber 26 through the transfer tube 52 without a second liquid drain outlet from the housing.

In the foregoing description, certain terms have been used for brevity, clearness, and understanding. No unnecessary limitations are to be implied therefrom beyond the requirement of the prior art because such terms are used for descriptive purposes and are intended to be broadly construed. The different configurations, systems, and method steps described herein may be used alone or in combination with other configurations, systems and method steps. It is to be expected that various equivalents, alternatives and modifications are possible within the scope of the appended claims. For example, other embodiments include first and second separator chambers 26 and 28, respectively, each of which may include an inertial impactor and/or a coalescer and/or a cyclone separator and/or other types of separators.

What is claimed is:

1. A coalescer comprising a housing having a separator chamber and a coalescer chamber, a separator in said separator chamber separating gas and liquid by inertial impaction, a coalescer filter element in said coalescer chamber separating gas and liquid by coalescence, said housing having a gas-liquid inlet delivering a gas-liquid mixture to said separator for at least partial pre-separation of said gas and liquid, said housing having a transfer passage transferring said partially pre-separated gas and liquid from said separator chamber to said coalescer chamber, at least a portion of said pre-separated liquid remaining in said separator chamber, said coalescer filter element dividing said coalescer chamber into an upstream subchamber and a downstream subchamber, said coalescer filter element having an upstream face facing said upstream subchamber and receiving said partially pre-separated gas and liquid through said transfer passage from said separator chamber, said coalescer filter element having a downstream face facing said downstream subchamber and discharging gas and separated coalesced liquid, the gas-liquid flow through said housing experiencing a pressure drop between said separator chamber and said downstream subchamber, said housing having a gas outlet discharging gas from said downstream subchamber, said housing having a drain outlet draining liquid from said downstream subchamber, a transfer tube extending between said separator chamber and said downstream subchamber and supplying said pre-separated liquid from said separator chamber through said transfer tube to said downstream subchamber as driven by the pressure differential between said separator chamber and said downstream subchamber, wherein said transfer tube is different than said transfer passage, said transfer passage has an inlet from said separator chamber, and an outlet to said upstream subchamber, said transfer tube has an inlet from said separator chamber, and an outlet to said downstream subchamber.

2. The coalescer according to claim 1 wherein:
said separator chamber has a sloped surface guiding said pre-separated liquid to a collection zone and forming a pool thereat;
said transfer tube has a lower end extending downwardly into said collection zone and submerged in said pre-separated liquid when said pool rises above a given level;
said transfer tube has an upper end communicating with said downstream subchamber.

3. The coalescer according to claim 1 wherein said drain outlet drains both:
a) coalesced liquid from said downstream face of said coalescer filter element along a first flow path through said downstream subchamber; and
b) pre-separated liquid from said separator along a second flow path through said separator chamber then through said transfer tube then through said downstream subchamber and joining said coalesced liquid along said first flow path.

4. The coalescer according to claim 1 wherein said pre-separated liquid is discharged from said separator chamber through said transfer tube without a second liquid drain outlet from said housing.

5. The coalescer according to claim 1 wherein said housing comprises a dividing wall between said separator chamber and said coalescer chamber, and said transfer passage and said transfer tube each extend through said dividing wall.

6. The coalescer according to claim 5 wherein said dividing wall has first, second and third openings therein, said first opening providing said transfer passage, said second opening being through said transfer tube, said third opening providing said drain outlet.

7. The coalescer according to claim 1 wherein:
said housing comprises a cover and a base;
said separator chamber is in said base;
said coalescer chamber is in said cover;
said drain outlet includes a drain passage through said base and isolated from said separator chamber.

8. The coalescer according to claim 7 wherein:
said housing comprises a dividing wall between said separator chamber and said coalescer chamber;
said dividing wall has a drain opening therein communicating with said downstream subchamber but not with said separator chamber;
liquid in said downstream subchamber drains through said drain opening in said dividing wall and through said drain passage through said base.

9. A crankcase ventilation filter for an internal combustion engine having blowby gas containing an air-oil mixture, comprising a housing having a separator chamber and a coalescer chamber, a separator in said separator chamber separating air and oil by inertial impaction, a coalescer filter element in said coalescer chamber separating air and oil by coalescence, said housing having an air-oil inlet delivering an air-oil mixture to said separator for at least partial pre-separation of said air and oil, said housing having a transfer passage transferring said partially pre-separated air and oil from said separator chamber to said coalescer chamber, at least a portion of said pre-separated oil remaining in said separator chamber, said coalescer filter element dividing said coalescer chamber into an upstream subchamber and a downstream subchamber, said coalescer filter element having an upstream face facing said upstream subchamber and receiving said partially pre-separated air and oil through said transfer passage from said separator chamber, said coalescer filter element having a downstream face facing said downstream subchamber and discharging air and separated coalesced oil, the air-oil flow through said housing experiencing a pressure drop between said separator chamber and said downstream subchamber, said housing having an air outlet discharging air from said downstream subchamber, said housing having an oil drain outlet draining oil from said downstream subchamber, a transfer tube extending between said separator chamber and said downstream subchamber and supplying said pre-separated oil to said downstream subchamber as driven by the pressure differential between said separator chamber and said downstream subchamber, wherein said transfer tube is different than said transfer passage, said transfer passage has an inlet from said separator chamber, and an outlet to said upstream subchamber, said transfer tube has an inlet from said separator chamber, and an outlet to said downstream subchamber.

10. The coalescer according to claim 9 wherein:
said separator chamber has a sloped surface guiding said pre-separated oil to a collection zone and forming a pool thereat;
said transfer tube has a lower end extending downwardly into said collection zone and submerged in said pre-separated oil when said pool rises above a given level;
said transfer tube has an upper end communicating with said downstream subchamber.

11. The coalescer according to claim 9 wherein said drain outlet drains both:
a) coalesced oil from said downstream face of said coalescer filter element along a first flow path through said downstream subchamber; and
b) pre-separated oil from said separator along a second flow path through said separator chamber then through said transfer tube then through said downstream subchamber and joining said coalesced oil along said first flow path.

12. The coalescer according to claim 9 wherein said pre-separated oil is discharged from said separator chamber through said transfer tube without a second oil drain outlet from said housing.

13. The coalescer according to claim 9 wherein said housing comprises a dividing wall between said separator chamber and said coalescer chamber, and said transfer passage and said transfer tube each extend through said dividing wall.

14. The coalescer according to claim 13 wherein said dividing wall has first, second and third openings therein, said first opening providing said transfer passage, said second opening being through said transfer tube, said third opening providing said drain outlet.

15. The coalescer according to claim 9 wherein:
said housing comprises a cover and a base;
said separator chamber is in said base;
said coalescer chamber is in said cover;
said drain outlet includes a drain passage through said base and isolated from said separator chamber.

16. The coalescer according to claim 15 wherein:
said housing comprises a dividing wall between said separator chamber and said coalescer chamber;
said dividing wall has a drain opening therein communicating with said downstream subchamber but not with said separator chamber;
oil in said downstream subchamber drains through said drain opening in said dividing wall and through said drain passage through said base.

17. A method for eliminating a second liquid drain outlet in a coalescer having a housing having a separator chamber and a coalescer chamber, with a separator in said separator chamber separating gas and liquid by inertial impaction, and a coalescer in said coalescer chamber separating gas and liquid by coalescence, said method comprising providing said housing with a gas-liquid inlet delivering a gas-liquid mixture to said separator for at least partial pre-separation of said gas and liquid, providing said housing with a transfer passage transferring said partially pre-separated gas and liquid from said separator chamber to said coalescer chamber, at least a portion of said pre-separated liquid remaining in said separator chamber, providing a coalescer filter element dividing said coalescer chamber into an upstream subchamber and a downstream subchamber, providing said coalescer filter element with an upstream face facing said upstream subchamber and receiving said partially pre-separated gas and liquid through said transfer passage from said separator chamber, providing said coalescer filter element with a downstream face facing said downstream subchamber and discharging gas and separated coalesced liquid, providing the gas-liquid flow through said housing to experience a pressure drop between said separator chamber and said downstream subchamber, providing said housing with a gas outlet discharging gas from said downstream subchamber, providing said housing with a drain outlet draining liquid from said downstream subchamber, providing a transfer tube extending between said separator chamber and said downstream subchamber, and supplying said pre-separated liquid from said separator chamber through said transfer tube to said downstream subchamber as driven by the pressure differential between said separator chamber and said downstream subchamber, wherein said transfer tube is different than said transfer passage, said transfer passage has an inlet from said separator chamber, and an outlet to said upstream subchamber, said transfer tube has an inlet from said separator chamber, and an outlet to said downstream subchamber.

18. The method according to claim 17 comprising providing said separator chamber with a sloped surface, guiding said pre-separated liquid along said sloped surface to a collection zone forming a pool thereat, providing said transfer tube with a lower end extending downwardly into said collection zone and submerged in said pre-separated liquid when said pool rises above a given level, and providing said transfer tube with an upper end communicating with said downstream subchamber.

19. The method according to claim 17 comprising draining through said drain outlet both:
a) coalesced liquid from said downstream face of said coalescer filter element along a first flow path through said downstream subchamber; and
b) pre-separated liquid from said separator along a second flow path through said separator chamber then through said transfer tube then through said downstream subchamber and joining with said coalesced liquid along said first flow path.

20. The method according to claim 17 comprising discharging said pre-separated liquid from said separator chamber through said transfer tube without a second liquid drain outlet from said housing.

21. A separator comprising a housing having first and second separator chambers separating gas and liquid, said housing having a gas-liquid inlet delivering a gas-liquid mixture to said first separator chamber for at least partial pre-separation of said gas and liquid, said housing having a transfer passage transferring said partially pre-separated gas and liquid from said first separator chamber to said second separator chamber, at least a portion of said pre-separated liquid remaining in said first separator chamber, the gas-liquid flow through said housing experiencing a pressure drop between said first separator chamber and second separator chamber, said housing having a gas outlet discharging gas from said second separator chamber, said housing having a drain outlet draining liquid from said second separator chamber, a transfer tube extending between said first and second separator chambers and supplying said pre-separated liquid from said first separator chamber through said transfer tube to said second separator chamber as driven by the pressure differential between said first separator chamber and said second separator chamber, wherein said transfer tube is different than said transfer passage.

22. The separator according to claim 21 wherein:
said first separator chamber has a sloped surface guiding said pre-separated liquid to a collection zone and forming a pool thereat;
said transfer tube has a lower end extending downwardly into said collection zone and submerged in said pre-separated liquid when said pool rises above a given level;
said transfer tube has an upper end communicating with said second separator chamber.

23. The separator according to claim 21 wherein said drain outlet drains both: a) separated liquid from said second separator chamber along a first flow path through said second separator chamber; and b) pre-separated liquid from said first separator chamber along a second flow path through said first separator chamber then through said transfer tube then through said second separator chamber and joining said separated liquid along said first flow path.

24. The separator according to claim 21 wherein said pre-separated liquid is discharged from said first separator chamber through said transfer tube without a second liquid drain outlet from said housing.

25. The separator according to claim 21 wherein said housing comprises a dividing wall between said first and second separator chambers, and said transfer passage and said transfer tube each extend through said dividing wall.

26. The separator according to claim 25 wherein said dividing wall has first and second openings therein, said first opening providing said transfer passage, said second opening being through said transfer tube.

27. The separator according to claim 21 wherein said first separator chamber includes an inertial impactor performing separation by inertial impaction, and said second separator chamber includes a coalescer performing separation by coalescence.

28. The separator according to claim 21 wherein said transfer passage has an inlet from said first separator chamber, and an outlet to said second separator chamber, said transfer tube has an inlet from said first separator chamber, and an outlet to said second separator chamber at a location spaced from and at a lower pressure than said outlet of said transfer passage.

* * * * *